US012185912B2

(12) United States Patent
English et al.

(10) Patent No.: US 12,185,912 B2
(45) Date of Patent: Jan. 7, 2025

(54) ELEVATOR COMPONENTS FOR MEDICAL DEVICES

(71) Applicant: Boston Scientific Scimed, Inc., Maple Grove, MN (US)

(72) Inventors: James English, Cahir (IE); Liam Ryan, Dungarvan (IE); Robert Hannon, Limerick (IE); Mark Mirigian, Piltown (IE); Adam Larouche, Worcester, MA (US); Steven Delfosse, Northborough, MA (US); Stephen Hale, Lismore (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 556 days.

(21) Appl. No.: 17/487,196

(22) Filed: Sep. 28, 2021

(65) Prior Publication Data

US 2022/0095890 A1    Mar. 31, 2022

Related U.S. Application Data

(60) Provisional application No. 63/084,593, filed on Sep. 29, 2020.

(51) Int. Cl.
| | | |
|---|---|---|
| *A61B 1/00* | (2006.01) | |
| *B33Y 10/00* | (2015.01) | |
| *B33Y 30/00* | (2015.01) | |
| *B33Y 80/00* | (2015.01) | |

(52) U.S. Cl.
CPC ........ *A61B 1/0011* (2013.01); *A61B 1/00098* (2013.01); *B33Y 10/00* (2014.12); *B33Y 30/00* (2014.12); *B33Y 80/00* (2014.12)

(58) Field of Classification Search
CPC ... A61B 1/0011; A61B 1/00098; B33Y 10/00; B33Y 30/00; B33Y 80/00
USPC ........................................................ 600/101
See application file for complete search history.

(56) References Cited

U.S. PATENT DOCUMENTS

| | | | | |
|---|---|---|---|---|
| 2014/0084517 | A1* | 3/2014 | Sperry | B29C 64/245 264/494 |
| 2019/0059702 | A1* | 2/2019 | Hosogoe | A61B 1/0011 |
| 2019/0202128 | A1* | 7/2019 | Winburne | B33Y 40/20 |

FOREIGN PATENT DOCUMENTS

WO    WO-2017025432 A1 *   2/2017    ......... A61B 1/00098

OTHER PUBLICATIONS

International Search Report and Written Opinion issued in International Application No. PCT/US2021/052296, issued Jan. 4, 2022 (13 pages).

* cited by examiner

*Primary Examiner* — Timothy J Neal
*Assistant Examiner* — James Edward Boice
(74) *Attorney, Agent, or Firm* — Bookoff McAndrews, PLLC

(57) ABSTRACT

A method of manufacturing an elevator of a medical device comprises using an additive manufacturing method, forming a pivot portion at a proximal end of the elevator. The pivot portion tapers proximally such that a proximalmost end of the elevator is thinner than more distal portions of the pivot portion. The method further comprises using the additive manufacturing method, forming a body of the elevator that is distal to the pivot portion. The elevator body includes a surface configured to contact an instrument inserted in a working channel of the medical device.

20 Claims, 5 Drawing Sheets

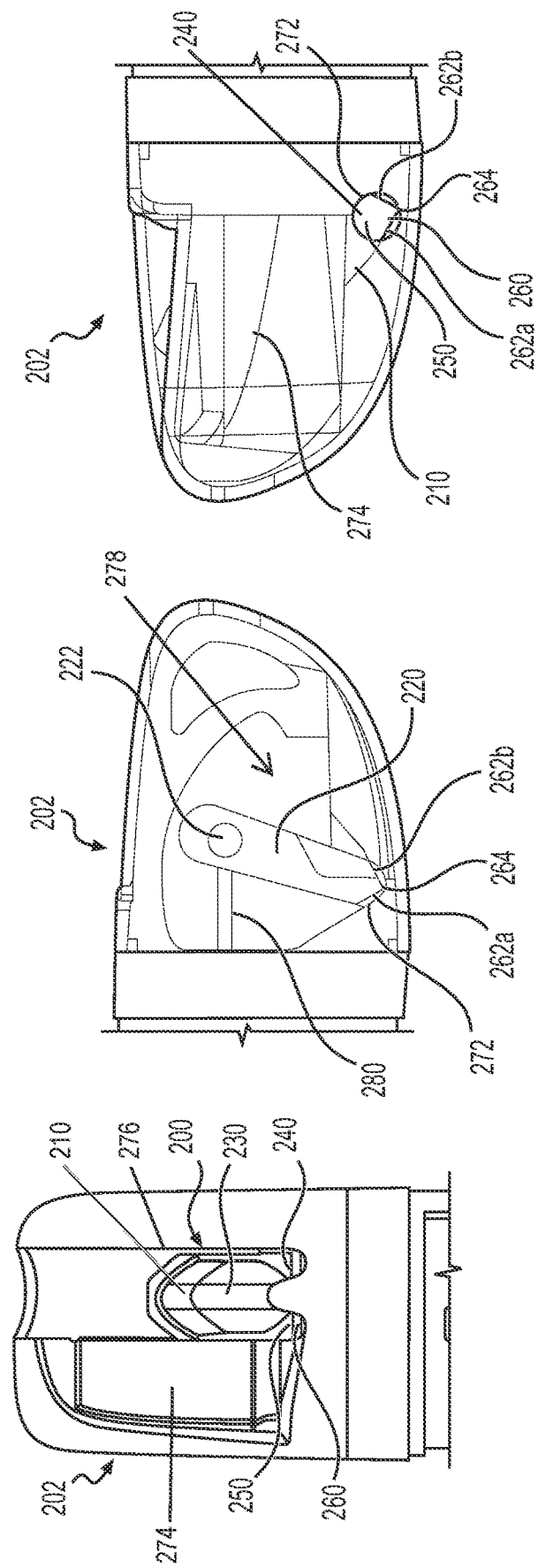

ELEVATOR COMPONENTS FOR MEDICAL DEVICES

CROSS-REFERENCE TO RELATED APPLICATIONS

This patent application claims the benefit of priority under 35 U.S.C. § 119 to U.S. Provisional Patent Application No. 63/084,593, filed Sep. 29, 2020, which is herein incorporated by reference in its entirety.

TECHNICAL FIELD

Various aspects of this disclosure relate generally to devices and methods for elevators of medical devices, and in particular to elevators constructed using additive manufacturing.

BACKGROUND

Duodenoscopes may include a distal tip portion, which may include features such as optical elements (e.g., camera, lighting), air/water outlets, and working channel openings. An elevator may be disposed at a distal tip and may be actuatable in order to change an orientation of a medical device/tool passed through the working channel. For example, the elevator may be pivotable or otherwise movable. The elevator may be controlled via a control mechanism in a handle, such as a lever, which may be attached to a control wire that attaches to the elevator.

SUMMARY

Each of the aspects disclosed herein may include one or more of the features described in connection with any of the other disclosed aspects.

A method of manufacturing an elevator of a medical device may comprise using an additive manufacturing method, forming a pivot portion at a proximal end of the elevator. The pivot portion may taper proximally such that a proximalmost end of the elevator is thinner than more distal portions of the pivot portion. The method may further comprise using the additive manufacturing method, forming a body of the elevator that is distal to the pivot portion. The elevator body may include a surface configured to contact an instrument inserted in a working channel of the medical device.

Any of the methods or devices disclosed herein may include any of the following features. The method may further comprise manually removing the elevator from a build platform. The additive manufacturing method may include powder bed fusion. The proximal end may form a proximal-facing face or a proximal edge. The method may further comprise: using the additive manufacturing method, forming a control arm of the elevator. The control arm may be configured to be connected to a control element for exerting a force on the elevator. The proximalmost end may extend along the body and the control arm. The proximalmost end may extend along an entirety of a width of the elevator. The method may further comprise: using the additive manufacturing method, forming a junction of the control arm and the body. An amount of energy applied to the junction may be greater than an amount of energy applied to at least a portion of the body. The junction may have a greater yield strength than the at least a portion of the body. Forming the control arm may include forming one or more hollow portions of the control arm.

In an example, an elevator for use with a medical device may be made according to the following process. Using an additive manufacturing method, a pivot portion may be formed at a proximal end of the elevator. The pivot portion may taper proximally such that a proximalmost end of the elevator is thinner than more distal portions of the pivot portion. Using the additive manufacturing method, a body of the elevator may be formed that is distal to the pivot portion. The elevator body may include a surface configured to contact an instrument inserted in a working channel of the medical device.

Any of the devices or methods disclosed herein may include any of the following features. The proximal end may form a proximal-facing face or a proximal edge. The process may further comprise: using the additive manufacturing method, forming a control arm of the elevator. The control arm may be configured to be connected to a control element for exerting a force on the elevator. The proximalmost end may extend along the body and the control arm. The proximalmost end may extend along an entirety of a width of the elevator.

In another example, an elevator for use with a medical device may include: an elevator body having a surface for interacting with a medical instrument inserted through a working channel of the medical device; a control arm configured to receive a control element for applying a force to the elevator; and a pivot portion proximal of the elevator body. The pivot portion may include a tapered portion having surfaces that taper inward in a proximal direction to a proximalmost surface of the elevator. The proximalmost surface may extend along a width of the elevator from an end of the elevator body to an end of the control arm.

Any of the devices or methods disclosed herein may include any of the following features. The proximalmost surface may be an edge. The pivot portion may include a portion having a rounded surface. The pivot portion may have a uniform cross section along a lateral axis of the elevator. The lateral axis may extend along the width of the elevator. The pivot portion may be solid in all cross-sections. A junction between the body and the control arm may have a greater yield strength than the at least the portion of the body. At least a portion of the control arm may be hollow.

In another example, an elevator for use with a medical device may include: an elevator body having a surface for interacting with a medical instrument inserted through a working channel of the medical device; and a pivot portion proximate of the elevator body. The pivot portion may include: a tapered portion having surfaces that taper inward in a proximal direction to a proximalmost surface of the elevator; and a rounded portion distal of the tapered portion. The rounded portion may have a rounded surface, and the pivot portion may be solid in all cross-sections. The elevator may further comprise a control arm. A junction between the body and the control arm may have a greater yield strength than the at least the portion of the body. At least a portion of the control arm may be hollow.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "diameter" may refer to a width where an element is not circular.

The term "distal" refers to a direction away from an operator, and the term "proximal" refers to a direction toward an operator. The term "exemplary" is used in the sense of "example," rather than "ideal." The term "approximately," or like terms (e.g., "substantially"), includes values +/−10% of a stated value.

BRIEF DESCRIPTION OF THE DRAWINGS

The accompanying drawings, which are incorporated in and constitute a part of this specification, illustrate aspects this disclosure and together with the description, serve to explain the principles of the disclosure.

FIGS. 3A-3C depict exemplary distal tips utilizing another exemplary elevator.

DETAILED DESCRIPTION

It may be desirable for an elevator to have low manufacturing costs, comply with tight manufacturing tolerances, and have sufficient strength to withstand pushing/pulling forces exerted on the elevator. Additive manufacturing (e.g., 3D metal printing) may facilitate cost-effective construction, as compared to molding or subtractive manufacturing techniques. For example, for manufacturing of single-use duodenoscopes, it may be particularly desirable to manufacture components, such as elevators, at lower costs and at larger scales. Powder bed fusion is a type of additive manufacturing technique that may be used to manufacture an elevator of an endoscope. Multiple elevators may be manufactured simultaneously, allowing for increased efficiency and lower cost. Techniques for additive manufacturing are discussed in further detail below.

In a step of an additive manufacturing techniques, components (e.g., one or more elevators) may be formed on a single substrate and may be removed from the substrate in a manufacturing step. In an example, an elevator may be manually removed (e.g., snapped or broken off) from the substrate, which may save time and manufacturing costs as compared to other methods. The elevator may be printed/additively manufactured so as to facilitate manual removal of the elevator (or other component). For example, an elevator may taper at one end, toward the substrate. The tapered end may terminate in a narrow edge, sufficiently narrow to permit manual separation of the elevator from the substrate. This narrow edge may contact a portion of the distal tip of the duodenoscope that receives the elevator. A shape of the narrow edge may limit wobble/other movement of the elevator within the distal tip, thereby facilitating better control of the elevator.

Figure 1:
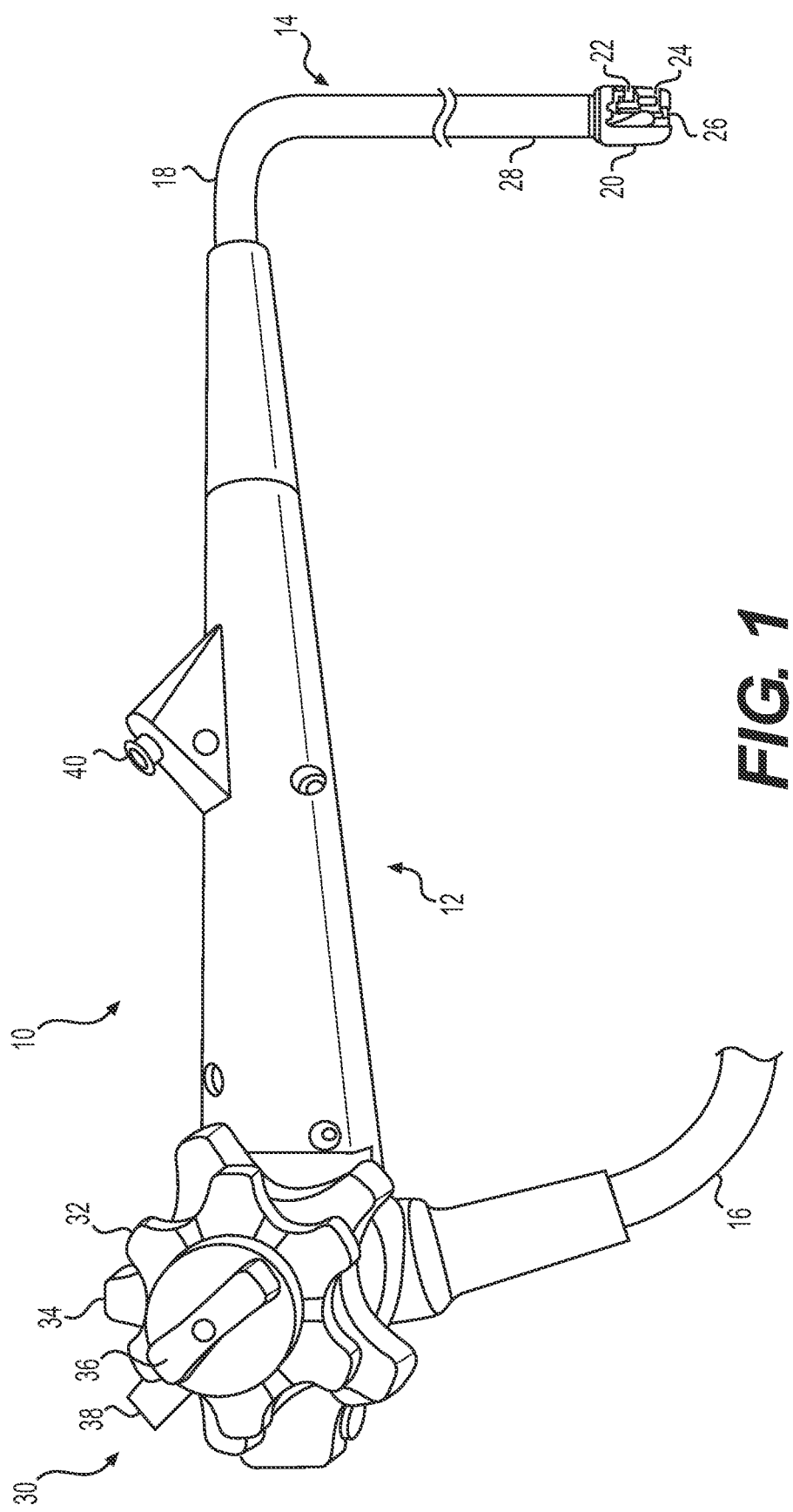
FIG. 1 depicts an exemplary duodenoscope.

FIG. 1 depicts an exemplary duodenoscope 10 having a handle 12 and an insertion portion 14. Duodenoscope 10 may also include an umbilicus 16 for purposes of connecting duodenoscope 10 to sources of, for example, air, water, suction, power, etc., as well as to image processing and/or viewing equipment. Although the term duodenoscope may be used herein, it will be appreciated that other devices, including, but not limited to, endoscopes, colonoscopes, ureteroscopes, bronchoscopes, laparoscopes, sheaths, catheters, or any other suitable delivery device or medical device that may include an elevator or a like distal tip component, may be used in connection with the devices and manufacturing methods of this disclosure. Although side-facing devices are particularly discussed, the embodiments described herein may also be used with front-facing endoscopes (e.g., endoscopes where a viewing element faces longitudinally forward).

Insertion portion 14 may include a sheath or shaft 18 and a distal tip 20. Distal tip 20 may include an imaging device 22 (e.g., a camera) and a lighting source 24 (e.g., an LED or an optical fiber). Distal tip 20 may be side-facing. That is, imaging device 22 and lighting source 24 may face radially outward, perpendicularly or approximately perpendicularly to a longitudinal axis of shaft 18 and distal tip 20.

Distal tip 20 may also include an elevator 26 for changing an orientation of a tool inserted in a working channel of duodenoscope 10. Elevator 26 may alternatively be referred to as a swing stand, pivot stand, raising base, or any suitable other term. Elevator 26 may be pivotable via, e.g., an actuation wire (e.g., control wire 280, shown in FIG. 3B, described below) or another control element.

A distal portion of shaft 18 that is connected to distal tip 20 may have a steerable section 28. Steerable section 28 may be, for example, an articulation joint. Shaft 18 and steerable section 28 may include a variety of structures which are known or may become known in the art. Example features of distal tip 20 are described in further detail with respect to FIGS. 2A-5, herein.

Handle 12 may have one or more control mechanisms 30. Control mechanisms 30 may provide control over steerable section 28 or may allow for provision of air, water, suction, etc. For example, handle 12 may include control knobs 32, 34 for left, right, up, and/or down control of steerable section 28. For example, one of knobs 32, 34 may provide left/right control of steerable section 28, and the other of knobs 32, 34 may provide up/down control of steerable section 28. Handle 12 may further include one or more locking mechanisms 36 (e.g., knobs or levers) for preventing steering of steerable section 28 in at least one of an up, down, left, or right direction. Handle 12 may include an elevator control lever 38. Elevator control lever 38 may raise and/or lower elevator 100, via connection between lever 38 and control wire 280 (FIGS. 3A-3C). A port 40 may allow passage of a tool through port 40, into a working channel of the duodenoscope 10, through shaft 18, to distal tip 20.

When used in a duodenoscope, such as duodenoscope 10, proximalmost outer surface 164 may serve as a contact point with a housing of a distal tip (e.g., distal tip 20), facilitating pivoting of elevator 100. Proximalmost outer surface 164 may be stationary relative to the housing and may serve as a pivot point of elevator 100. Tapered surfaces 162a, 162b and/or proximalmost outer surface 164 may contact surfaces of a housing of the distal tip. Alternatively, proximalmost outer surface 164 may move (e.g., slide or rotate) relative to the housing, and another portion of pivot portion 140 may serve as a pivot point for duodenoscope 10.

Figure 2B:
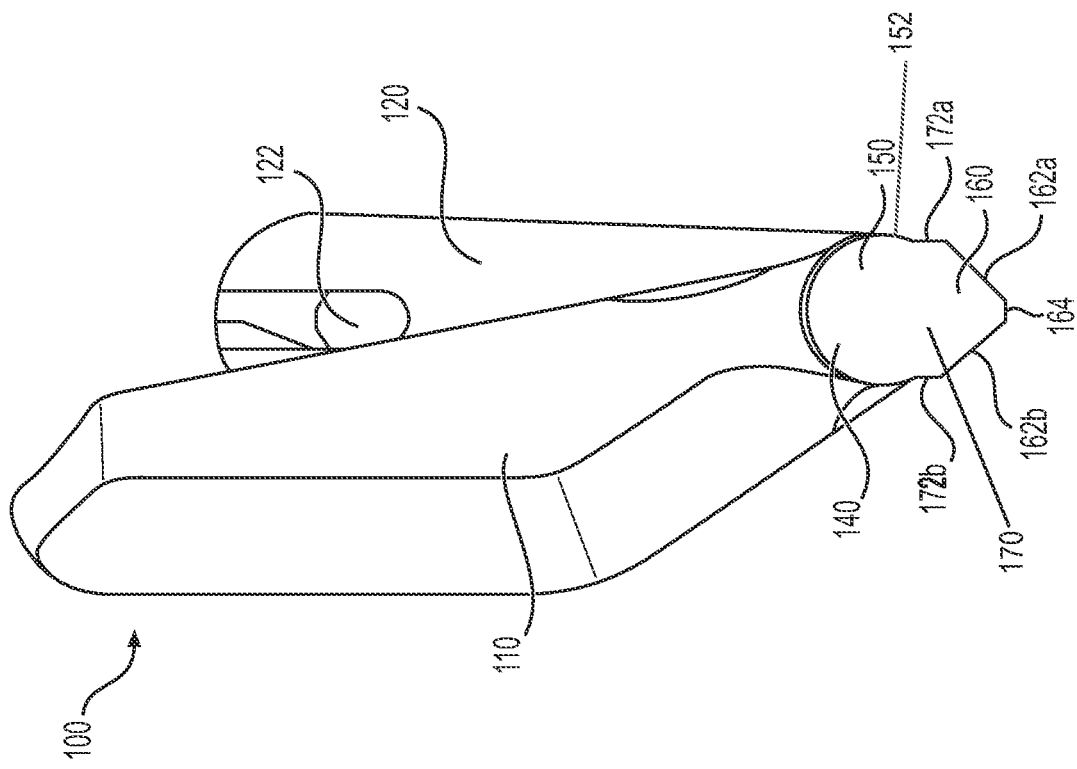
FIGS. 2A and 2B depict an exemplary elevator for use with the duodenoscope depicted in FIG. 1.
Figure 2A:
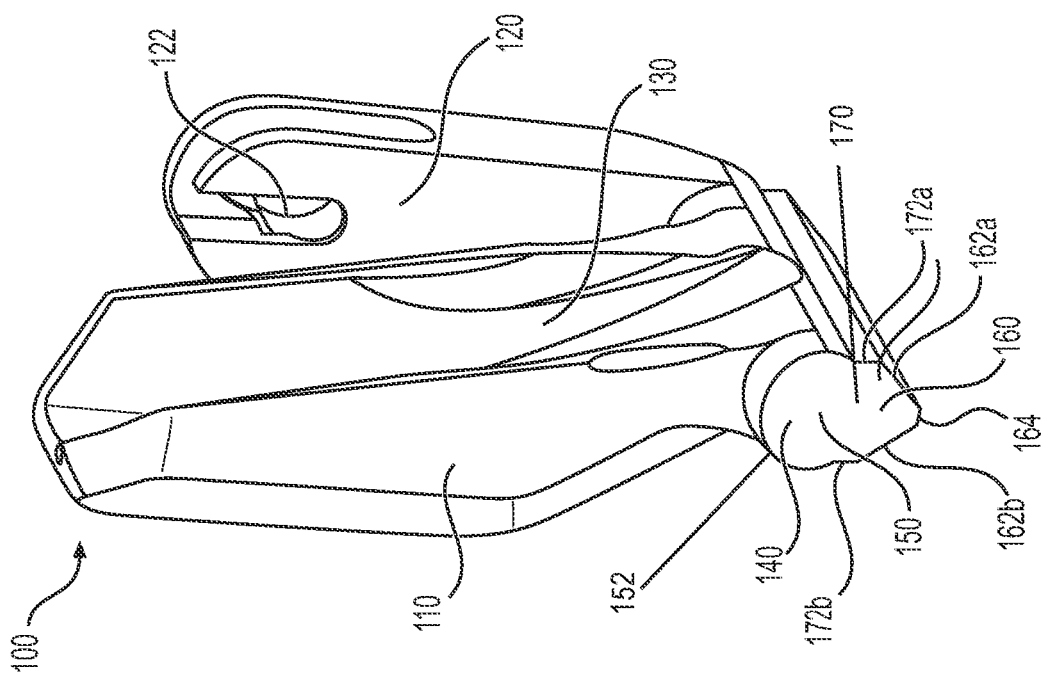

FIGS. 2A and 2B depict an exemplary elevator 100, which may have any of the properties of elevator 26 and may be used with components of duodenoscope 10. Features of any of the example elevators described below may be combined with one another. FIG. 2A shows a perspective view of elevator 100, and FIG. 2B shows a side view of elevator 100. When cross-sectional shapes of portions of elevator 100 are discussed below, the side view of FIG. 2B provides illustration of those cross-sectional shapes. When describing elevator 100, the following conventions will be used: a width of elevator 100/lateral direction of elevator 100 may be defined as the direction into/out of the page in FIG. 2B. A depth of elevator 100 may be defined as the left/right direction in FIG. 2B. A length of elevator 100/longitudinal direction of elevator 100 may be defined as extending up/down in FIG. 2B. A longitudinal axis of elevator 100 as a whole may extend in the longitudinal direction, described above. However, different portions of elevator 100 may have different longitudinal axes that may be referred to herein. For example, a proximal portion of elevator body 110 (described in further detail below) may have a different longitudinal axis than a distal portion of elevator body 110 (the proximal portion may be angled with respect to the distal portion).

Elevator 100 may be constructed using additive manufacturing techniques. For example, elevator 100 may be formed using powder bed fusion ("PBF") methods. In PBF, fine layers of metal powder may be deposited, and a laser may selectively sinter/fuse two-dimensional slices of a desired component (e.g., a top layer of the powder) until a three-dimensional component is fully built. Alternative heat sources may be used (e.g., a thermal print head, or other heat source). Powder in other areas of the powder bed may remain loose. Alternatively, elevator 100 may be formed according to other additive manufacturing techniques, including, for example, fused filament fabrication (i.e. fused deposition modeling), binder jetting, or other techniques.

Figure 5:
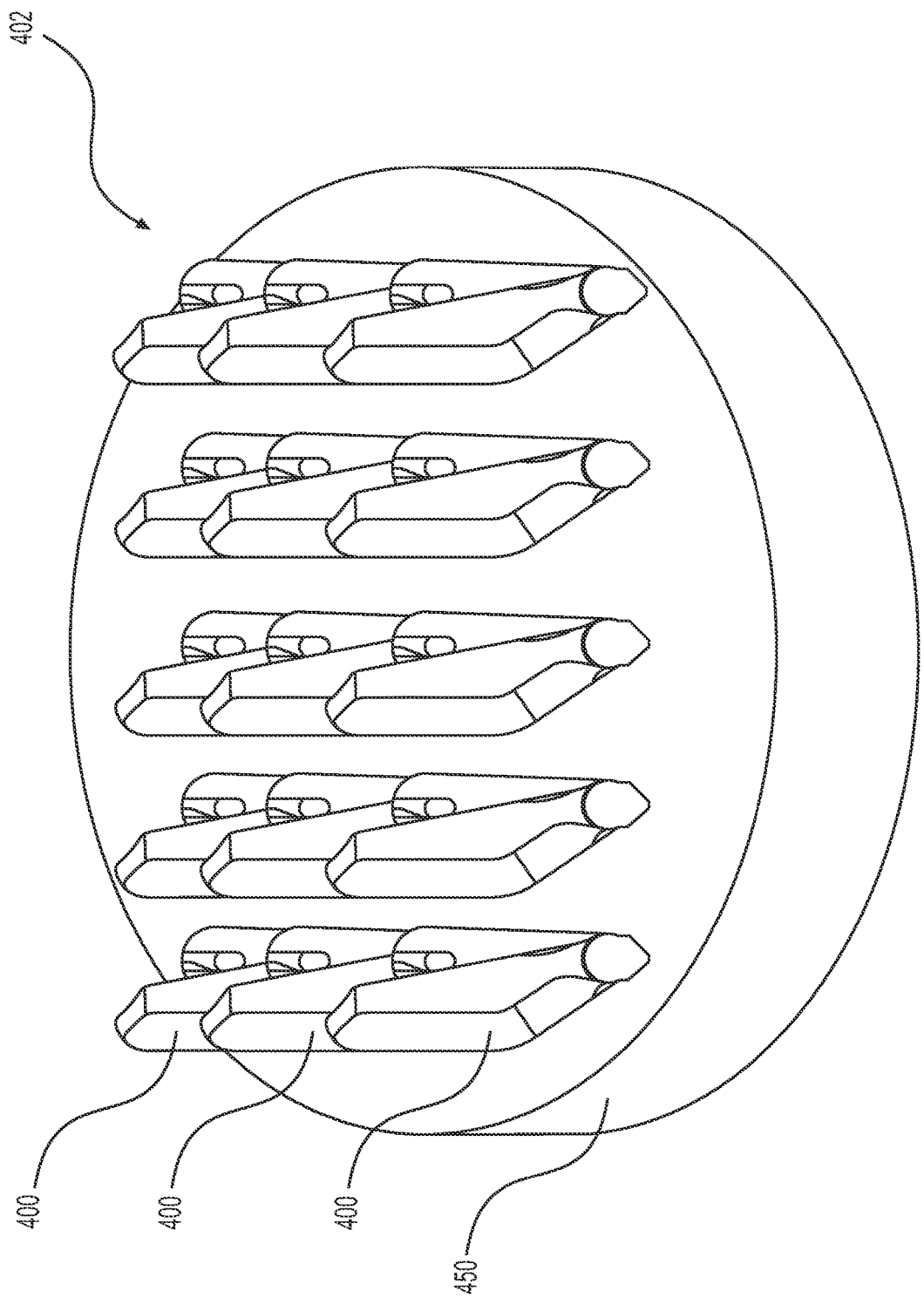
FIG. 5 depicts an exemplary substrate/build plate having a plurality of elevators, such as those depicted in FIGS. 2A-4, above, positioned thereon.

In PBF, manufactured components may be welded or otherwise attached to a substrate (e.g., a build platform), and/or supports. The substrate may have many copies of a component welded thereon (numerous copies of a part may be manufactured at the same time, as shown in FIG. 5, below). The substrate may provide support and structure for the components during the manufacturing process. However, the substrate may not form a portion of the desired end component and may require removal prior to use of the component or assembly of the component into a finished device. For example, electrical discharge machining ("EDM") or a computer numerical control ("CNC") machine may be used to cut the component from the substrate. Given that numerous components may be printed on the same substrate, the time dedicated to using, for example, a wire EDM to remove the components from the substrate may be large. For example, time using an EDM machine may be two-thirds or more of the time required for the PBF printing process. Thus, using EDM or other methods to cut the components from the substrate may be less efficient from a time and/or cost perspective.

It will be appreciated that further processing steps (e.g., debinding, sintering) may follow or be interspersed with any of the additive manufacturing methods described herein.

Elevator 100 may be manufactured according to specifications that allow manufacture without the use of an EDM or CNC machine to remove elevator 100 from a substrate on which it is additively manufactured. For example, elevator 100 may be manufactured so that it may be manually removed (e.g., broken off) from a substrate/build platform on which it is additively manufactured. In an example manufacturing process, elevator 100 may be additively manufactured using, e.g., PBF. Then, elevator 100 may be broken off from a substrate, which may also carry additional copies of elevator 100 (and/or other components). Other post-processing steps (e.g., debinding, sintering, polishing, sanding, etc.) may occur.

As shown in FIGS. 2A and 2B, elevator 100 may include an elevator body 110 and a control arm 120. Control arm 120 may include a receptacle 122 for receiving a control wire (or other control element) to be used to raise and/or lower elevator 100. Receptacle 122 may include, for example, a hole and/or a slot. As shown in FIG. 2B, control arm 120 and elevator body 110 may be offset from one another along a depth of elevator 100 (e.g., control arm 120 and elevator body 110 may have different central longitudinal axes).

Elevator body 110 may include a tool-engaging surface 130 for interacting with (e.g., contacting) and changing an orientation of a tool inserted into a working channel of a duodenoscope, such as duodenoscope 10. Rotational motion of tool-engaging surface 130 (details of accomplishing such rotation are described below) may deflect a medical tool (e.g., a forceps, catheter, clip, snare, or other suitable tool) by, for example, bending a shaft of the medical tool proximally. Use of elevator 100 to change an orientation of the tool may facilitate access to a biliary tract of a subject.

Pivot portion 140 may facilitate movement of elevator body 110 and control arm 120. For example, elevator 100 may pivot about pivot portion 140. A portion of pivot portion 140 may contact a surface of a housing of distal tip 20, as described in further detail below. During the additive manufacturing process, elevator 100 may be connected to a substrate/printing plate via pivot portion 140. Pivot portion 140 may be a portion of elevator 100 which is broken off from the substrate. Pivot portion 140 may be shaped so as to facilitate breaking off elevator 100 manually from the substrate/build platform.

Pivot portion 140 may include a rounded portion 150 and a tapered portion 160. A cross-section of pivot portion 140 may be the same/identical/uniform along a lateral axis of pivot portion 140 (along a width of elevator 100). Alternatively, a cross-section of pivot portion 140 may vary along the lateral axis of pivot portion 140 (along a width of elevator 100).

Rounded portion 150 may form a portion of a cylinder (e.g., may resemble a cylinder with a cutout at a proximal end of rounded portion 150). Rounded portion 150 may have a cross-section that is a portion of a circle, and have a rounded/circular outer surface 152. Rounded portion 150 may be a distal end of pivot portion 140. Although rounded portion 150 is described as having circular characteristics, rounded portion 150 may be ovular, ovoid, or have another round shape. Alternatively, rounded portion 150 may be omitted.

Tapered portion 160 may have a triangular prism or trapezoidal prism shape. Tapered portion 160 may have a cross-sectional shape that is triangular or trapezoidal, as shown in FIGS. 2A-2B. Where tapered portion 160 has a trapezoidal cross-sectional shape, the cross-section may resemble a triangle with the point flattened/removed. As shown in FIGS. 2A and 2B, tapered portion 160 may include two tapered outer surfaces 162a, 162b that taper radially inward in a proximal direction. Tapered surfaces 162a, 162b may taper inward at the same angle. Tapered portion 160 may also include a proximalmost surface 164. A face of proximal surface 164 may be approximately perpendicular to a longitudinal axis of control arm 120. Proximalmost surface 164 may be thinner (have less depth) than more distal portions of pivot portion 140, to facilitate releasing proximalmost surface 164 from a substrate/build plate. Proximalmost surface 164 may extend along an entire width of the elevator body 110 and the control arm 120, as well as an entire depth of elevator body 110/control arm 120.

Tapered portion 160 may be directly connected to rounded portion 150 (see FIGS. 3A-3C, described in further detail below). Alternatively, a rectangular portion 170 (having a rectangular cross-section and a rectangular prism shape) may connect rounded portion 150 to tapered portion 160. Rectangular portion 170 may have approximately parallel outer surfaces 172a, 172b, which may be approximately perpendicular to proximalmost surface 164 and approximately parallel to a longitudinal axis of control arm 120.

Therefore, when viewed in cross-section or in parallel, pivot portion 140 may have a proximalmost outer surface 164 which terminates in tapered outer surfaces 162a, 162b. Tapered outer surfaces 162a, 162b, in turn, may terminate in approximately parallel outer surfaces 172a, 172b. Approximately parallel outer surfaces 172a, 172b may terminate in rounded surface 152.

Surfaces of pivot portion 140 on either lateral end of elevator 100 may be approximately parallel to one another. Alternatively, one or both of those surfaces may be tapered laterally inward in a proximal direction, laterally outward in a proximal direction, may be curved, or may have another suitable profile. Alternatively to the tapered portion 160, described above, a proximal end of elevator 100 may include a necked proximal end (a portion that is narrow but not necessarily tapered) to facilitate removal of the elevator from the substrate/build plate.

When used in a duodenoscope, such as duodenoscope 10, proximalmost outer surface 164 may serve as a contact point with a housing of a distal tip (e.g., distal tip 20), facilitating pivoting of elevator arm 100. Proximalmost outer surface 164 may be stationary relative to the housing and may serve as a pivot point of elevator 100. Tapered surfaces 162a, 162b and/or proximalmost outer surface 164 may contact surfaces of a housing of the distal tip. Alternatively, proximalmost outer surface 164 may move (e.g., slide or rotate) relative to the housing, and another portion of pivot portion 140 may serve as a pivot point for endoscope 100.

Elevator 100 may be formed of a single, integrated piece by additive manufacturing, as described above. Elevator 100 may provide for pivoting of elevator 100 without the use of, for example, a pivot pin. Pivot portion 140 may be solid in all cross-sections, with no holes formed therein. Instead, the distal housing of duodenoscope 10 and elevator 100 may be configured to provide for pivoting of elevator 100. For example, a shape of the housing and pivot portion 140 of elevator 100 may be complementary such that the housing receives/mates with pivot portion 140. For example, one or more lateral sides of pivot portion 140 may snap fit into the housing. Alternatively, any other mechanism or relationship between pivot portion 140 and the housing may facilitate pivoting/rotation of elevator 100. The only components of the distal tip (e.g., distal tip 20) used to raise and lower elevator may be elevator 100, the housing of the distal tip, a pull wire, and any structure used to secure the pull wire to control arm 120.

Elevator 100 may have features to facilitate visualization of treatment tools during a medical treatment. For example, control arm 120 may be hollow or partially hollow (e.g., include an internal lattice structure) in order to permit visualization of a tool inserted through a working channel of an endoscope (e.g., duodenoscope 10). If control arm 120 is formed of solid, radiopaque material, control arm 120 may block a view of the tool when viewed on, for example, fluoroscopy. Although control arm 120 is provided as an example of a component that may be constructed to be at least partially hollow and facilitate visualization of a procedure, other portions of elevator 100 may additionally or alternatively be at least partially hollow. Constructing portions of elevator 100 (e.g., control arm 120) so that they are hollow (or latticed) may also cut down on manufacturing time, increasing cost efficiency.

FIGS. 3A-3C show an elevator 200 (which may have any of the properties of elevator 100) positioned within a housing 202 of a distal tip of an endoscope (e.g., distal tip 20 of duodenoscope 10). Like reference numbers are used to reference corresponding elements of elevators 100 and 200 when possible. Elevator 200 may include an elevator body 210, having a tool-engaging surface 230, which may have any of the properties of elevator body 110, and tool-engaging surface 130, respectively. The terms (e.g., "lateral," "width," "depth") used to describe dimensions of elevator 200 are the same as those used for elevator 100, above.

Elevator 200 may also include a control arm 220 (having any of the properties of control arm 120) having a receptacle 222 (with any of the properties of receptacle 122). As shown in FIG. 3B, a control wire 280 may be secured to and/or within receptacle 222. Movement of control wire 280 proximally or distally (left/right in FIG. 3B) may exert a force on a distal end of control arm 220, which thereby exerts a force on a remainder of elevator 200, including elevator body 210. The force on the distal end of control arm 220 may cause elevator 200 to pivot about pivot portion 240, as described in further detail above and below.

Pivot portion 240 may have any of the properties of pivot portion 140, described above, except as described below. Where there are differences between pivot portions 240 and 140, it will be appreciated that features of pivot portions 140, 240 may be mixed and matched, and that elevator 100/pivot portion 140 may operate with housing 202 as described below for elevator 200/pivot portion 240.

Pivot portion 240 may have a rounded portion 250, which may have any of the properties of rounded portion 150. Pivot portion 240 may also have a tapered portion 260, which may have any of the properties of tapered portion 160.

Tapered portion 260 may have a triangular prism shape. Tapered portion 260 may have a cross-sectional shape that is triangular, as shown in FIGS. 3B and 3C. Tapered portion 260 may include two tapered outer surfaces 262a, 262b that taper radially inward in a proximal direction. Outer surfaces 262a, 262b may taper inwardly at the same angle. Tapered portion 260 may also include a proximal point 264 on a proximalmost end of elevator 200. Proximal point 264 may form an edge in a lateral direction of elevator 200.

As most clearly shown in FIG. 3C, pivot portion 240 may have a general shape of a triangle with one rounded side (the distal side of the triangle), opposite proximal point 264. In other words, tapered portion 260 may have a triangle shape, and rounded portion 250 may have a shape that is a segment of a circle, where the depth of the proximal portion of the segment of the circle of rounded portion 250 is the same as the depth of the distal end of tapered portion 260.

Pivot portion 240 may fit within a hole or recess 272 of housing 202. Recess 272 may have, for example, a circular shape. Recess 272 may extend across a width of a portion of housing 202 in which elevator 200 is received. Alternatively, recess 272 may be disposed only at one or more lateral ends of pivot portion 240. Recess 272 may have a varying shape. For example, recess 272 may be circular at one end of recess 272 and then may have an arcuate shape (with open sides) at other portions of recess 272.

As shown in FIG. 3A, one side of elevator body 210 may be adjacent to a block 274 holding optical elements (e.g., camera and lighting). The other side of elevator body 210 may be adjacent to a wall 276. Wall 276 may partially define a cavity 278 in which control arm 220 may be received.

When elevator 200 is pivoted/rotated by control wire 280, proximal point 264 may serve as a pivot point and remain stationary. Alternatively, proximal point 264 may rotate, and another portion of pivot portion 240 (or another portion of elevator 200) may remain stationary.

Elevator 200 may be manufactured according to any of the methods described above, with respect to elevator 100. For example, elevator 200 may be manufactured with an additive manufacturing technique, such as PBF. Elevator 200 may contact a substrate/build platform at point 264, and point 264 may form a break-off point for elevator 200 from the substrate/build platform. Therefore, use of cutters such as an EDM machine, may not be necessary.

Elevators 100 and 200 may be attached to a substrate/build platform via a "perforated" junction. For example, proximal facing surface 164/point 264 may have spans that are welded to the substrate/build platform interspersed with spans that are not welded to the substrate/build platform to form a "perforated" junction. Including spans that are not welded to the substrate/build platform may make it easier to manually break off elevator 100 or 200 from the substrate/build platform. After breaking off elevator 100/200, proximal facing surface 164/point 264 may have a serrated surface.

Features of pivot portions 140, 240 may facilitate a close fit between pivot portion 140, 240 and housing 202 of a distal tip (e.g., recess 272 of housing 202). If instead of the profiles described herein, a pivot portion were round, designed to fit within a round recess (e.g., recess 272), the shape of the round pivot portion would need to be ideal and/or have support within the recess. A surface of housing 202 of the distal tip (e.g., recess 272 of housing 202) may be shaped so as to complement the shape of pivot portion 140, 240. As compared with a round pivot portion, pivot portions 140, 240 engage more effectively with a recess (e.g., recess 272). Effective engagement with the recess (e.g., recess 272) may facilitate movement of the elevator only in a desired manner (e.g., rotation about pivot portion 140, 240). This is due at least in part to the fact that referencing errors are more likely to occur with round pivot portions than pivot portions shaped like pivot portions 140, 240. A flat proximal surface (e.g., proximalmost surface 164) may provide a more effective reference for setting the elevator to a specific, desired angle than a rounded surface provides. Tighter adherence to manufacturing tolerances by pivot portions 140, 240 may result in less rattle and/or slop of elevator 100, 200, respectively, thereby providing better control of elevator 100, 200, respectively.

Figure 4:
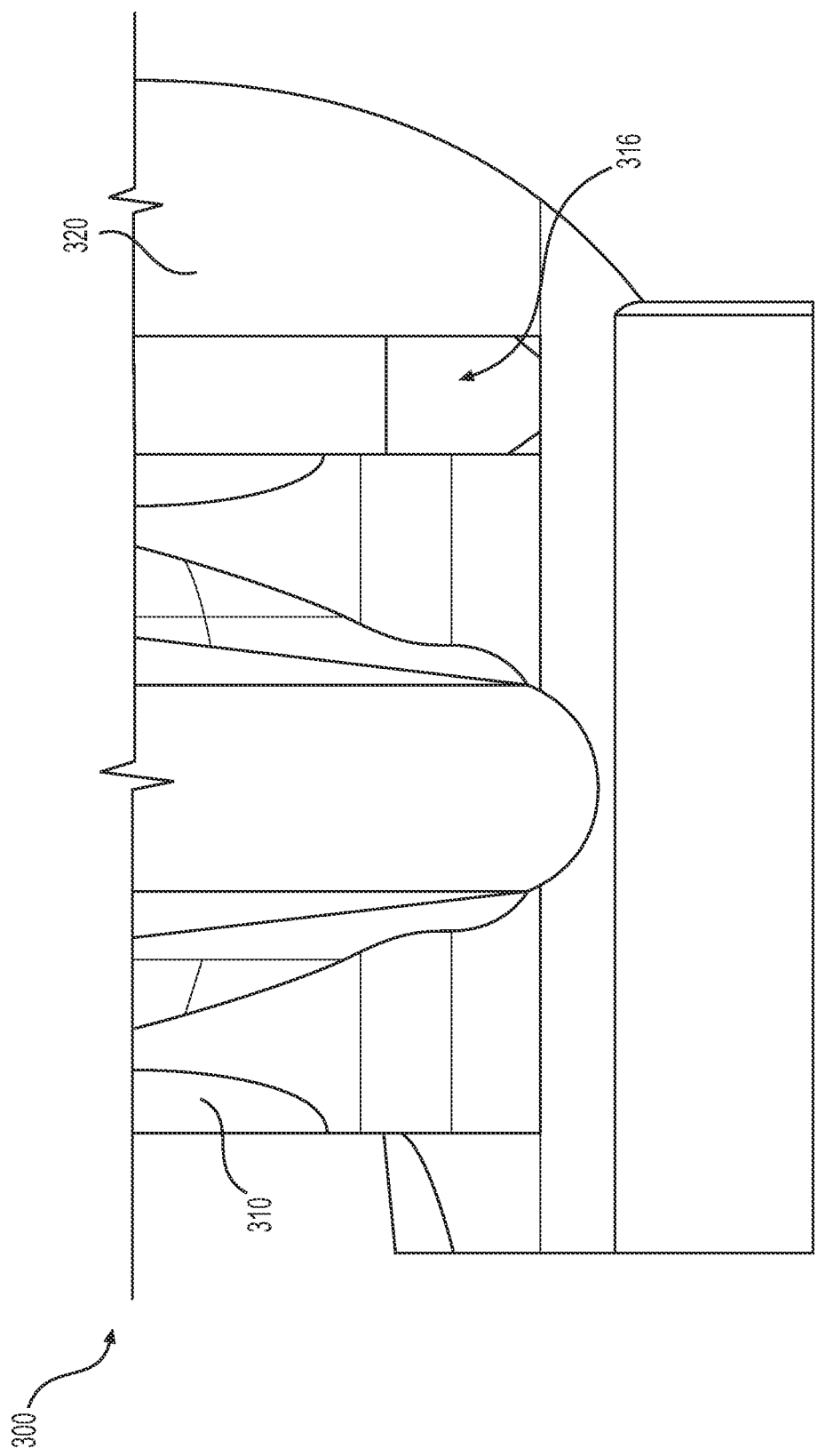
FIG. 4 depicts a portion of an exemplary elevator having any of the features of the elevators depicted in FIGS. 2A-3C.

FIG. 4 depicts a proximal portion of an elevator 300, which may have any of the characteristics of elevators 26, 100, and/or 200. Elevator 300 may include an elevator body 310 and a control arm 320. Elevator body 310 and control arm 320 may join at a junction 316. Junction 316 may be manufactured according to techniques to optimize or increase a strength of junction 316 and/or control arm 320. During use, control arm 320 may be subject to large amounts of stress, and manufacturing techniques may be chosen to increase strength of junction 316 and to prevent bending/twisting/torsion of control arm 320 relative to elevator body 310.

For example, using PBF techniques, laser parameters may be chosen to obtain a smooth surface of elevator body 310, control arm 320, and/or junction 316. The laser parameters may prevent, minimize, or otherwise inhibit formation of pearls (raised areas) on a surface of elevator 300. Such pearls may interfere with engagement between elevator 300 and components such as a body of a distal tip (e.g., housing 202) or a pull wire (e.g., pull control wire 280).

Junction 316 may be manufactured so as to have a high ductility and a high yield strength, as compared to elevators manufactured with other techniques (e.g., machined elevators). For example, additional energy (e.g., additional laser energy in PBF) may be applied to junction 316 to provide for increased yield strength, as compared to a remainder of elevator 300 or to other types of elevators. Junction 316 may also have a higher yield strength than other portions of elevator 300 (e.g., elevator body 310 or control arm 320)

A method for manufacturing an elevator (e.g., elevator 26, 100, 200, or 300) may include additively manufacturing the elevator (using, e.g., PBF). The elevator may be manufactured such that a proximal end of the elevator (e.g., pivot portion 140, 240) is fused to or otherwise fixed to a substrate/build platform. The elevator may be manufactured according to a specification that provides that the proximal end (e.g., the pivot portion) tapers to a smaller depth in a proximal direction (e.g., terminating in proximal-facing surface 164 or point 264), such that a small surface area is fused to the substrate/build plate. A shape of the proximal end (e.g., the pivot portion) may be, for example, pyramid or approximately triangular prism shaped. This shape may facilitate manually removing (e.g., breaking off) the elevator from the substrate/build platform. An operator may manually remove the elevator, rather than cutting off the elevator with a cutting device such as an EDM, which may reduce manufacturing time and/or complexity.

A layer of powder may be deposited to form a proximal portion of the elevator (e.g., proximal-facing surface 164 or point 264), adjacent to a substrate/build platform. The first formed layer of the elevator may be narrow/lack depth to facilitate breaking the elevator off from the substrate. Subsequent layers of powder may be deposited to form more distal portions of the elevator. For example, to form tapered portions (e.g., tapered portion 160, 260), progressively broader portions of layers of powder may be sintered/fused. A distal tip of the elevator may be the last portion of the elevator that is formed.

FIG. 5 shows an assembly 502 showing a plurality of elevators 400 on a substrate/build plate 450. As shown in FIG. 5, a plurality of elevators 400 (which may have any of the properties of elevators 26, 100, 200, 300) may be manufactured/printed on a single substrate or build plate 450. Manufacturing of a plurality of elevators 400 on a single substrate may increase manufacturing efficiency and lower cost by allowing the simultaneous manufacture of multiple components. Such increased efficiency may be particularly desirable in the case of manufacturing single-use duodenoscopes, which each requires separate elevators. Because manufacturing of single-use devices may involve manufacture of more total devices, such efficiencies may be particularly useful. The elevators 400 may be identical to one another or may differ from one another. Elevators 400 may be arranged in any suitable manner (e.g., in a grid having multiple rows and/or columns of elevators 400). Substrate 450 may have any suitable shape. Each elevator 400 may have a break-off portion 484. In order to remove elevators 400 from substrate 450, a human or machine may manually break off, knock off, or otherwise remove elevator 400 from substrate 450. Elevators 400 may be individually removed or may be removed together. For example, a force may be applied to remove a plurality (some, a majority, or all) of elevators 400 from substrate 450 simultaneously, near simultaneously, or at a similar time. The force may be applied at a suitable angle (e.g., at an angle to the up/down direction shown in FIG. 5, with at least a component of the force applied parallel to substrate 450). Additionally or alternatively, vibrational or other types of forces may be used to remove one or more of elevators 400 from substrate 450.

While principles of this disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A method of manufacturing an elevator of a medical device, the method comprising:
    using an additive manufacturing method, forming a pivot portion at a proximal end of the elevator, wherein the pivot portion tapers proximally such that a proximalmost end of the elevator is thinner than more distal portions of the pivot portion, wherein the proximalmost end forms a proximal-facing face or a proximal edge; and
    using the additive manufacturing method, forming (i) a body of the elevator that is distal to the pivot portion and (ii) a control arm of the elevator, the control arm having one or more hollow portions, wherein the body includes a surface configured to contact an instrument inserted in a working channel of the medical device, and wherein the control arm is configured to be connected to a control element for exerting a force on the elevator.

2. The method of claim 1, further comprising manually removing the elevator from a build platform.

3. The method of claim 1, wherein the additive manufacturing method includes powder bed fusion.

4. The method of claim 1, wherein the proximalmost end extends along the body and the control arm.

5. The method of claim 4, wherein the proximalmost end extends along an entirety of a width of the elevator.

6. The method of claim 1, further comprising:
    using the additive manufacturing method, forming a junction of the control arm and the body, wherein an amount of energy applied to the junction is greater than an amount of energy applied to at least a portion of the body.

7. The method of claim 6, wherein the junction has a greater yield strength than at least a portion of the body.

8. A method of manufacturing an elevator of a medical device, the method comprising:
    using additive manufacturing, forming a pivot portion at a proximal end of the elevator, wherein the pivot portion tapers proximally to a proximalmost surface or a proximalmost edge;
    using additive manufacturing, forming a body of the elevator that is distal to the pivot portion, wherein the body includes a surface configured to contact an instrument inserted in a working channel of the medical device; and
    using additive manufacturing, forming a control arm of the elevator, wherein the control arm is configured to receive a distal end of a control element for exerting a force on the elevator, wherein the control arm includes one or more hollow portions.

9. The method of claim 8, wherein the additive manufacturing includes powder bed fusion.

10. The method of claim 8, wherein the pivot portion includes a first tapered surface and a second tapered surface, and wherein each of the first and second tapered surfaces taper inward at a same angle.

11. The method of claim 8, wherein a distal end of the pivot portion includes a rounded portion.

12. The method of claim 11, wherein the pivot portion further includes a rectangular portion, wherein the rectangular portion connects the rounded portion to the pivot portion that tapers, and wherein the rectangular portion includes a pair of parallel surfaces that are perpendicular to a longitudinal axis of the control arm.

13. The method of claim 8, wherein the proximalmost surface extends along an entire width of the body and the control arm.

14. The method of claim 8, wherein the body defines a first longitudinal axis, and wherein the control arm defines a second longitudinal axis, wherein the first longitudinal axis and the second longitudinal axis extend in different directions.

15. The method of claim 14, wherein the proximalmost surface of the pivot portion is perpendicular to the second longitudinal axis.

16. The method of claim 8, wherein the control arm includes a receptacle defined at the distal end of the control arm, and wherein the control element is received within the receptacle.

17. A method of manufacturing an elevator of a medical device, the method comprising:
    forming a pivot portion at a proximal end of the elevator, wherein the pivot portion is formed on a build platform;
    forming a body of the elevator, wherein the body includes a surface configured to contact a medical instrument inserted in a working channel of a medical device;
    forming a control arm of the elevator, wherein the control arm is configured to receive a distal end of a control element for exerting a force on the elevator, and wherein the control arm includes one or more hollow portions; and
    removing the elevator from the build platform.

18. The method of claim 17, wherein the pivot portion includes a rectangular portion, a rounded portion, and a tapered portion, wherein the rectangular portion connects the rounded portion to the tapered portion, and wherein the rectangular portion includes a pair of parallel surfaces that are perpendicular to a longitudinal axis of the control arm.

19. The method of claim 17, wherein the pivot portion includes a first tapered surface and a second tapered surface, and wherein each of the first and second tapered surfaces taper towards one another at a same angle.

20. The method of claim 17, wherein the pivot portion includes a proximalmost surface or a proximalmost edge that extends along an entire width of the body and the control arm.

* * * * *